United States Patent
Przybylo et al.

(10) Patent No.: US 11,759,424 B2
(45) Date of Patent: *Sep. 19, 2023

(54) HIGH-EFFICIENCY ENCAPSULATION OF HYDROPHILIC COMPOUNDS IN UNILAMELLAR LIPOSOMES

(71) Applicant: LIPID SYSTEMS SP. Z.O.O., Wroclaw (PL)

(72) Inventors: Magdalena Przybylo, Wroclaw (PL); Marek Langner, Wroclaw (PL); Tomasz Borowik, Cracow (PL)

(73) Assignee: LIPID SYSTEMS SP. Z.O.O., Wroclaw (PL)

( * ) Notice: Subject to any disclaimer, the term of this patent is extended or adjusted under 35 U.S.C. 154(b) by 0 days.

This patent is subject to a terminal disclaimer.

(21) Appl. No.: 17/857,302

(22) Filed: Jul. 5, 2022

(65) Prior Publication Data

US 2022/0331250 A1    Oct. 20, 2022

Related U.S. Application Data

(62) Division of application No. 16/496,780, filed as application No. PCT/EP2018/057400 on Mar. 23, 2018, now Pat. No. 11,426,349.

(30) Foreign Application Priority Data

Mar. 23, 2017 (EP) .................. 17162568

(51) Int. Cl.
*A61K 9/127* (2006.01)
*A61K 47/10* (2017.01)

(52) U.S. Cl.
CPC .......... *A61K 9/1272* (2013.01); *A61K 9/1277* (2013.01); *A61K 47/10* (2013.01)

(58) Field of Classification Search
CPC .................................................. A61K 9/1272
See application file for complete search history.

(56) References Cited

FOREIGN PATENT DOCUMENTS

WO    1989/00812      2/1989
WO    2010/102770 A1  9/2010

OTHER PUBLICATIONS

Dordelmann et al (J. Mater. Chem. B, 2014, 2, 7250-7259). (Year: 2014).*
Zhao, et al., (Dec. 2016) "Using PG-Liposome-based system to enhance puerarin Liver-targeted therapy for alcohol-induced liver disease," AAPS PharmSciTech, 17(6): 1376-1382.

(Continued)

*Primary Examiner* — Benjamin J Packard
(74) *Attorney, Agent, or Firm* — McDonnell Boehnen Hulbert & Berghoff

(57) ABSTRACT

The present invention relates to high-efficiency encapsulation of hydrophilic substances in the hydrophilic space of unilamellar liposomes. High-efficiency encapsulation is achieved by the use of a polyhydric alcohol selected from propylene glycol or glycerine for dissolving the hydrophobic compounds forming the lipid bilayer of the liposomes. The invention provides unilamellar liposomes (UL) as well as a method for preparing same by way of low temperature extrusion. The invention also relates to use of these UL in the manufacturing of a medicament, a cosmetic product, a food additive or a disinfectant.

19 Claims, 6 Drawing Sheets

(56) References Cited

OTHER PUBLICATIONS

Figure 1:
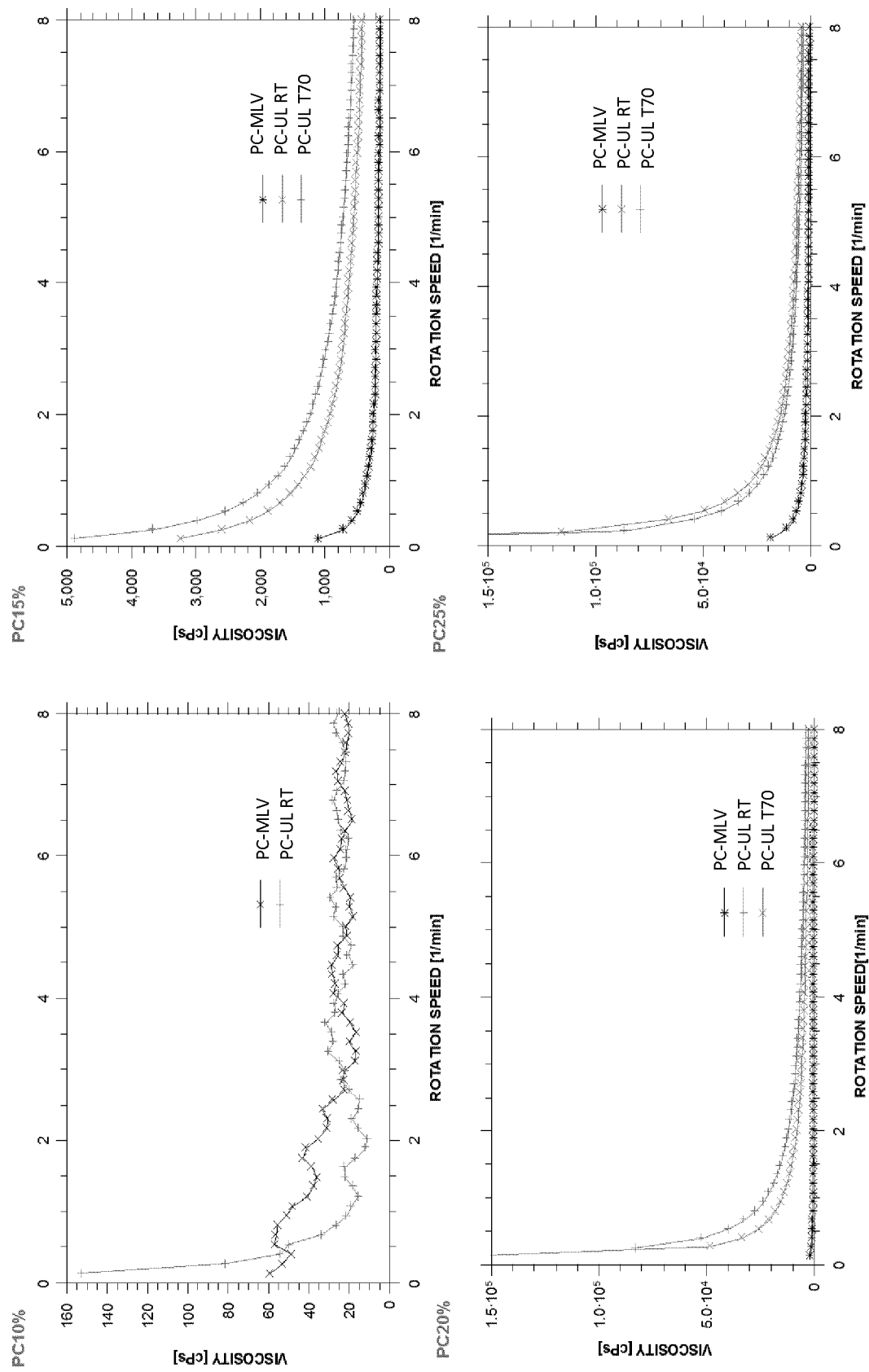

Office Action for JP2020-501593, dated Jun. 28, 2021, with English translation.
The International Search Report (ISR) with Written Opinion for PCT/EP2018/057400 dated Jun. 8, 2018, pp. 1-14.
Elmoslemany, Riham M. et al. "Propylene Glycol Liposomes as a Topical Delivery System for Miconazole Nitrate: Comparison with Conventional Liposomes" AAPS PharmSciTech (2012) vol. 13(2), pp. 723-731.
Manconi, M. et al. "Development and characterization of liposomes containing glycols as carriers for diclofenac" Colloids and Surfaces A: Physicochemical and Engineering Aspects (2009) vol. 342(1-3), pp. 53-58.
Manca, Maria Letizia et al. "Glycerosomes: A new tool for effective dermal and transdermal drug delivery" International Journal of Pharmaceutics (2013), pp. 66-74.
Kulmarni, et al., "Factors affecting microencapsulation of drugs in liposomes," J.Microencapsulation, 12(3): 229-246. 1995.
Ringhieri, et al., "The influence of liposomal formulation on the incorporation and retention of PNA oligomers," Colloids and Surfaces B: Biointerfaces, 145: 462-469, 2016.
Roy, et al., "Influence of lipid composition, pH, and temperature on physiochemical properties of liposomes with curcumin as model drug," J. Oleo Sci, 65(5): 399-411, 2016.

\* cited by examiner

HIGH-EFFICIENCY ENCAPSULATION OF HYDROPHILIC COMPOUNDS IN UNILAMELLAR LIPOSOMES

CROSS-REFERENCE TO RELATED APPLICATION

This application is a divisional application of U.S. patent application Ser. No. 16/496,780, filed Sep. 23, 2019, which is a U.S. national phase entry of International Application No. PCT/EP2018/057400, filed Mar. 23, 2018, which claims priority to European Patent Application No. 17162568.4 filed Mar. 23, 2017, all of which are incorporated by reference herein in their entirety.

FIELD OF THE INVENTION

The present invention relates to the field of pharmaceutical technology and in particular to high-efficiency liposomal encapsulation of hydrophilic substances. More specifically, the present invention relates to unilamellar liposomes (UL) with one lipid bilayer enclosing a hydrophilic space, wherein said hydrophilic space comprises at least one hydrophilic compound, and to a liquid composition comprising such unilamellar liposomes. The invention also relates to a method for encapsulation of hydrophilic compounds in unilamellar liposomes (UL) and to the use of these UL in the manufacturing of medicaments, cosmetic products, food additives or disinfectant.

BACKGROUND OF THE INVENTION

Liposomes are small vesicles having a membrane consisting of a lipid bilayer—similar to a cell membrane—which encloses a hydrophilic space. Characteristic is the amphiphilic character of the membrane molecules, which possess a hydrophilic head and a hydrophobic tail. Within the membrane of the liposomes, the amphiphilic molecules are arranged in such way that the hydrophilic parts are in contact with the aqueous environment inside and outside the liposome while the hydrophobic parts are located within the double layer. The membrane molecules are connected to one another by non-covalent interactions. Liposomes have either one or more lipid double layers and can have a size between 25 nm and 100 µm. The shape and size of the vesicles inter alia depend on the properties of the surrounding aqueous phase, the exact chemical composition of their membrane and their production method.

Liposomes are commonly used in pharmacological and cosmetic formulations, for instance in order to increase the solubility of amphiphilic and hydrophobic compounds, which results in an increase of their bioavailability (see e. g. Kshirsagar, N. A., Pandya, S. K., Kirodian, B. G., and Sanath, S. (2005) *Liposomal drug delivery system from laboratory to clinic.*, J. Postgrad. Med. 51, S5-S15; or Kalhapure, R. S., Suleman, N., Mocktar, C., Seedat, N., and Govender, T. (2015) *Nanoengineered Drug Delivery Systems for Enhancing Antibiotic Therapy*, J Pharm Sci-Us 104, 872-905). Using liposomes as a drug delivery system facilitates targeted and selective transport of said drug to the relevant sites in the human organism. This reduces side effects of the liposomally formulated drug and increases efficiency and therapeutic breadth, since lower doses can be administered.

Basically, a liposomal formulation is open to most compounds due to the special physicochemical characteristics of the liposome. In an aqueous liposomal dispersion substances with a high partition coefficient are only found within the lipid bilayer, regardless of their topology or the size of the liposomes, whereas substances with a low partition coefficient may be dispersed or diluted in the aqueous dispersion medium or encapsulated within the hydrophilic space of the liposomes.

Nevertheless, at present, the actual therapeutic use of liposome-enclosed hydrophilic compounds is insignificant due to the lack of a universal method for high-efficiency encapsulation of hydrophilic substances in liposomes. Passive encapsulation, which involves preparing liposomes by hydration of a dry lipid film by shaking with an aqueous solution containing the hydrophilic compound to be encapsulated, yields a very low encapsulation efficiency, which often does not exceed a few percent. In addition, the liposomes obtained by this method are multilamellar vesicles (MLVs), which largely vary in size and topology (see e.g. WO 01/13887, EP 1 565 164). The passive encapsulation method can be modified by subjecting the hydrated lipid dispersion to a homogenization process (see e.g. EP 0 776 194 A1, PL396706 A1, PL399298 A1, PL388134 A1 and PL399592 A1) or sonication (see e.g. PL389430 A1; or Watwe, R. M., and Bellare, J. R. (1995) *Manufacture of Liposomes—a Review*, Curr Sci India 68, 715-724) in order to produce smaller, more uniformly sized suspensions. However, these techniques typically lead to a suspension of low viscosity, which lacks structuration of the aqueous dispersion medium by the lipid structures, which in turn results in a poor encapsulation efficiency. Typically, only about 5-15% of the total hydrophilic drug added to the lipid film is encapsulated in the vesicles. Moreover, the high energy applied during homogenization or sonication causes instabilities of the liposome suspension due to oxidation, and increases the risk of functional degradation of sensitive active substances such as proteins or supramolecular assemblies.

Another group of techniques for liposomal encapsulation of hydrophilic compounds uses a mixture of substances with different polarities. However, these techniques are not suitable for the encapsulation of most of the proteins or other complex molecular structures, since the non-polar solvents used in these techniques irreversibly alter the structure of such molecules. Further, encapsulation efficiency of these techniques is not satisfactory either. For instance, EP 0 514 435 B1 discloses a method for preparing a liposomal gel composition, wherein phospholipids (15-30 wt %) are dissolved by shaking an aqueous solution containing a monohydroxy alcohol in an amount of 14-20% by weight, and the resulting liposomes are loaded with hydrophilic compounds by homogenization. This method cannot be expected to cause structuration of the aqueous phase with the lipid vesicle membranes, which makes the encapsulation efficiency low, while monohydroxy alcohols have denaturing and irritant properties. DE 40 03 783 A1 describes a method for preparing liposomal dispersions by vigorously mixing phospholipids of vegetable origin in concentrations of up to 30% by weight in the presence of a monohydroxy alcohol (ethanol or 2-propanol) in an amount of 15-20% by weight. Also in this case the resulting aqueous liposome-containing dispersion is not structured, and encapsulation efficiency is expected to be low. A further drawback of this method is that the liposomes formed by mixing are heterogeneous in size.

Altering the polarity of an aqueous solution which allows for the formation of liposomes can also be achieved by using halogenated hydrocarbons as a solvent (WO 96/40061 A1) or injecting lipids dissolved in a chlorofluorocarbon solvent ("Freon") into an aqueous solution at high temperature (U.S.

Pat. No. 4,752,425). However, none of these methods yields an encapsulation efficiency of the hydrophilic substance of greater than 50%. Furthermore, high temperatures have to be applied for solvent evaporation, which prevents the use of said methods for encapsulating proteins and supramolecular complexes.

Further alternative techniques for encapsulating hydrophilic substances in liposomes involve complexing hydrophilic, highly electrostatically charged particles of the active substance with amphiphilic counter ions. As a result, an amphiphilic complex is formed, which is then covered with lipids. This method requires manipulation of mixtures with different polarities which is technologically difficult. Further, it can be applied only to highly charged molecules, i.e. nucleic acids (e.g. see Oh, Y. K., and Park, T. G. (2009) *siRNA delivery systems for cancer treatment*, Adv Drug Deliv Rev 61, 850-862), and is not suitable for encapsulating proteins that denature in the presence of hydrophobic liquids.

In an attempt to significantly increase encapsulation efficiencies of hydrophilic purine nucleosides and to obtain high intraliposomal drug concentrations WO 95/15762 discloses a process for the preparation of liposomal formulations comprising forming multilamellar liposomes containing vidarabine (or derivative) and subjecting the liposomes to lyophilization, controlled rehydration and, optionally, extrusion under pressure. However, after extrusion a maximum encapsulation efficiency of only 45% was reached.

Accordingly, it is an object of the present invention to provide liposomes comprising hydrophilic compounds, as well as a method for preparing such liposomes, which liposomes and method largely overcome the above-discussed problems of the prior art.

More specifically, it is an object of the invention to provide liposomes which stably encapsulate large amounts of hydrophilic compounds regardless of their further physicochemical properties such as size or charge, e.g. including ions, proteins, peptides, carbohydrates, natural and synthetic polymers, nucleic acids, and nucleic acid derivatives that denature in the presence of hydrophobic liquids.

It is also an object of the present invention to provide a method for encapsulating such hydrophilic compounds into the hydrophilic space of liposomes with an encapsulation efficiency of up to 100%. These objects are surprisingly met by the present invention.

SUMMARY OF THE INVENTION

In a first aspect, the present invention provides a unilamellar liposome (UL) with one lipid bilayer enclosing a hydrophilic space, wherein the UL comprises: (i) at least one hydrophobic compound forming the lipid bilayer, and (ii) propylene glycol or glycerine, and wherein the hydrophilic space comprises at least one hydrophilic compound dissolved in a hydrophilic solvent, and wherein the concentration of the hydrophilic compound in the hydrophilic solvent is at least 80% of the saturation concentration of the hydrophilic compound in the hydrophilic solvent at 20° C. and 101 kPa.

In an embodiment of the UL according to the first aspect, the weight ratio of the at least one hydrophobic compound forming the lipid bilayer and propylene glycol or glycerine is in the range of from 2:1 to 1:1.

In a further embodiment of the UL according to the first aspect, the weight ratio of the at least one hydrophobic compound forming the lipid bilayer and the at least one hydrophilic compound is in the range of from 100:1 to 1:3, from 50:1 to 1:2, or from 25:1 to 1:1.

In a further embodiment of the first aspect of the invention, the UL comprises the at least one hydrophobic compound in an amount from 15 to 40%, from 16 to 39%, from 17 to 38%, from 18 to 37%, from 19 to 35%, from 20 to 30%, from 21 to 25%, or from 22 to 24% by weight of the UL, and preferably from 20 to 40% by weight of the UL.

In a further embodiment of the UL according to the first aspect, the at least one hydrophilic compound is selected from the group consisting of: (i) low molecular weight hydrophilic substances having a molecular weight of from 100 Da to 1500 Da, from 200 Da to 1400 Da, from 300 Da to 1200 Da, or from 500 Da to 1000 Da; and (ii) hydrophilic macromolecules having a molecular weight range of from 1500 Da to 300 kDa, from 2 kDa to 280 kDa, from 5 kDa to 250 kDa, from 10 kDa to 200 kDa or from 50 kDa to 200 kDa.

In a further embodiment of the UL according to the first aspect, the at least one hydrophilic compound is selected from the group consisting of ions, proteins, peptides, carbohydrates, natural and synthetic polymers, nucleic acids, nucleic acid derivatives, and combinations thereof.

In a further embodiment of the UL according to the first aspect, the saturation concentration of the hydrophilic compound in the hydrophilic solvent is in the range from 1 g to 500 g per 1000 ml hydrophilic solvent, preferably in the range of 10 g to 200 g.

In a further embodiment of the UL according to the first aspect, the hydrophilic solvent is selected from the group consisting of water, aqueous buffer, aqueous salt solution, aqueous mono- or di-saccharide solution and combinations thereof.

In a second aspect, the present invention provides a method for encapsulation of hydrophilic compounds in ULs, said method comprising the following steps: (a) providing a lipid solution comprising at least one hydrophobic compound and a polyhydric alcohol selected from propylene glycol and glycerine; (b) providing an aqueous phase comprising at least one hydrophilic compound; (c) preparing a hydrated lipid solution by mixing the lipid solution of (a) with the aqueous phase of (b); and (d) extruding the hydrated lipid solution of (c) at a temperature of less than 80° C., wherein the at least one hydrophobic compound forms a homogenous population of ULs, wherein said ULs comprise more than 50% of the total volume of the aqueous phase.

In an embodiment of the method according to the second aspect, the at least one hydrophilic compound is encapsulated within the ULs with an encapsulation efficiency selected from at least 50%, at least 55%, at least 60%, at least 65%, at least 70%, at least 75%, at least 80%, at least 85%, at least 90%, at least 95%, at least 98%; or at least 99%.

In a further embodiment of the method according to the second aspect, the polyhydric alcohol is comprised in the hydrated lipid solution of step (c) in a concentration of from 5 to 30%, from 10 to 25%, from 15 to 22%, or from 18 to 20% by weight of the hydrated lipid solution.

In a further embodiment of the method according to the second aspect, the overall concentration of the at least one hydrophobic compound in the hydrated lipid solution of step (c) is from 15 to 40%, from 16 to 39%, from 17 to 38%, from 18 to 37%, from 19 to 35%, from 20 to 30%, from 21 to 25%, or from 22 to 24% by weight of said hydrated lipid solution, and preferably from 20 to 40% by weight of said hydrated lipid solution.

In a further embodiment of the method according to the second aspect, the at least one hydrophobic compound is selected from phospholipids, sphingolipids or sterols, preferably from phosphatidycholine, and more preferably from purified soybean phosphatidylcholine.

In a further embodiment of the method according to the second aspect, step (b) comprises adjusting the pH of the aqueous phase, preferably to a pH within the range of from 5.0 to 7.5, from 6.0 to 7.4, or from 7.0 to 7.2.

In a further embodiment, step (d) comprises extruding the hydrated lipid solution of (c) at a temperature of less than 60° C., less than 40° C., or less than 30° C., and, preferably, at 20° C.

In a further embodiment, the method according to the second aspect comprises a further step (e), wherein the polyhydric alcohol selected from propylene glycol and glycerine is removed from the extruded hydrated lipid solution resulting from step (d), preferably wherein said polyhydric alcohol is removed from said extruded hydrated lipid solution by ultrafiltration.

In a third aspect, the present invention provides a UL prepared by the method according to the second aspect of the present invention.

In a fourth aspect, the present invention provides a liquid composition comprising at least one UL according to the first or third aspect of the present invention.

In an embodiment of said fourth aspect, the liquid composition has at least one of the following properties: (i) a pH within the range of from 5.0 to 7.5, from 6.0 to 7.4, or from 7.0 to 7.2; (ii) an osmolarity in the range of from 30 mOsm to 400 mOsm, from 40 mOsm to 300 mOsm, or from 50 mOsm to 200 mOsm; (iii) a total molar ratio of the hydrophilic compounds to the hydrophobic compounds of between 10-5 and 1. In a preferred embodiment, said liquid composition is an aqueous composition.

In a further embodiment of the fourth aspect of the invention, the liquid composition further comprises at least one excipient, preferably wherein said excipient is selected form the group consisting of: buffering agents, osmotically active agents, preservatives, antioxidants, flavoring agents, aromatic agents, and combinations thereof; preferably wherein said osmotic agents are selected from monovalent salts or sugars, more preferably from sodium chloride and sucrose.

In a fifth aspect, the present invention relates to the UL according to the first or third aspect, or the composition according to the fourth aspect, for use in therapy.

In a sixth aspect, the present invention relates to a use of the UL according to the first or third aspect, or the composition according to the fourth aspect as a medicament, a cosmetic product, a food additive or a disinfectant.

FIGURES

FIG. 1: Graphical representation of changes in viscosity as a function of spindle speed. The graphs illustrate the results from the rheometer measurements described in Example 8. The tested liposome samples comprised different lipid concentrations (10, 15, 20, 25% by weight) and were obtained by use of different extrusion parameters. PC10%: lipid concentration in the sample prior to extrusion of 10% by weight of said sample; PC15%: lipid concentration in the sample prior to extrusion of 15% by weight of said sample; PC20%: lipid concentration in the sample prior to extrusion of 20% by weight of said sample; PC25%: lipid concentration in the sample prior to extrusion of 25% by weight of said sample; PC-MLV: non-extruded sample; PC-UL RT: sample extruded at room temperature, PC-UL T70: sample extruded at 70° C.

Figure 2:
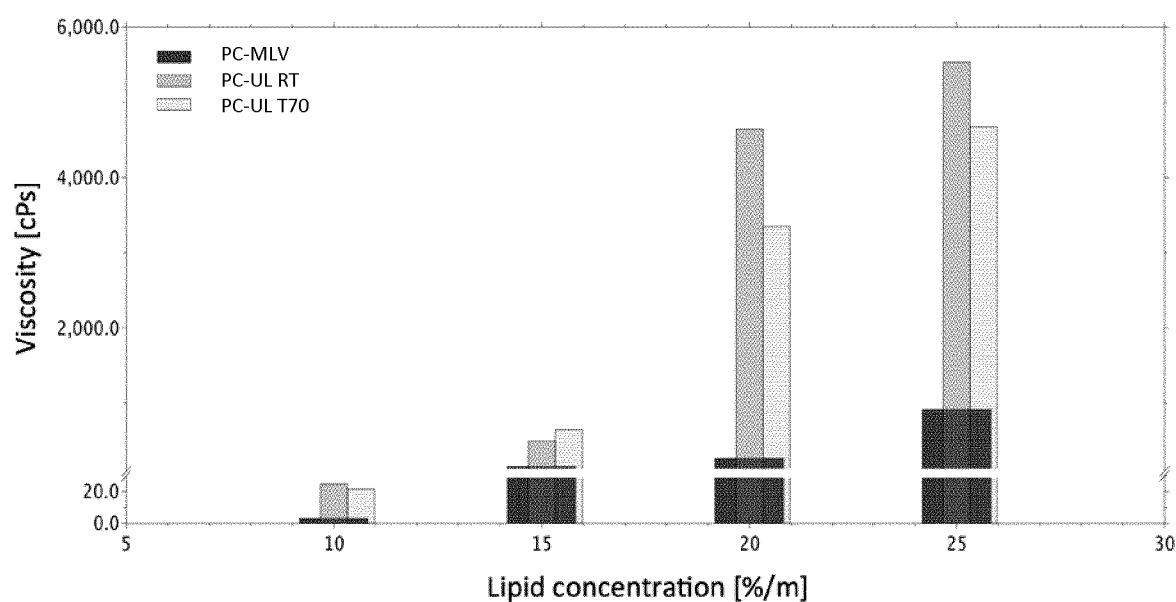

FIG. 2: Graphical representation of viscosity values as a function of lipid concentration. The graph illustrates the results obtained by the rheometer measurements described in Example 8. The tested liposome samples comprised different lipid concentrations (10%, 15%, 20%, 25% by weight of the sample) and were obtained by use of different extrusion parameters. For details see the description of FIG. 1.

Figure 3A:
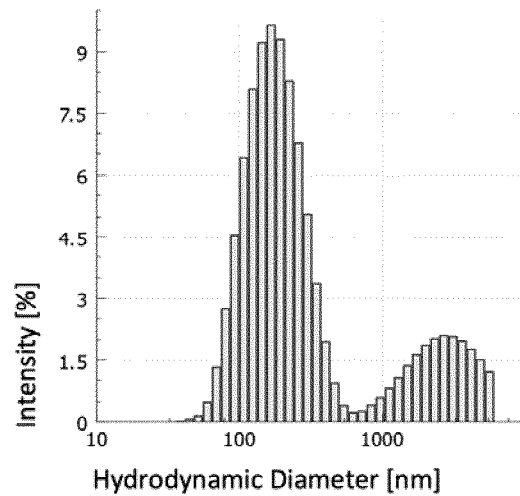
Figure 3A:
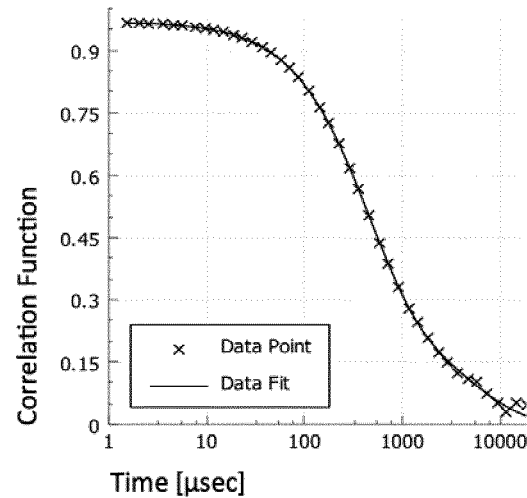
Figure 3B:
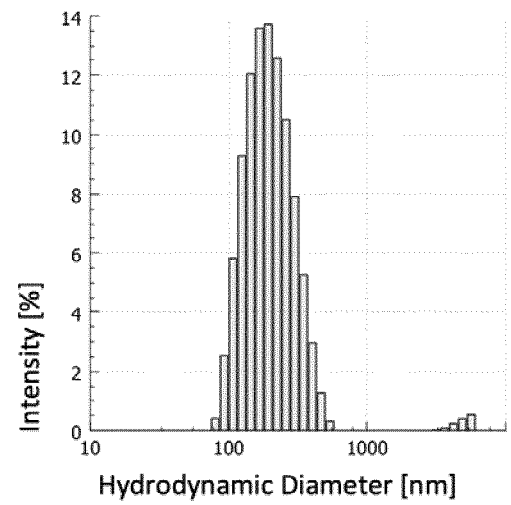
Figure 3B:
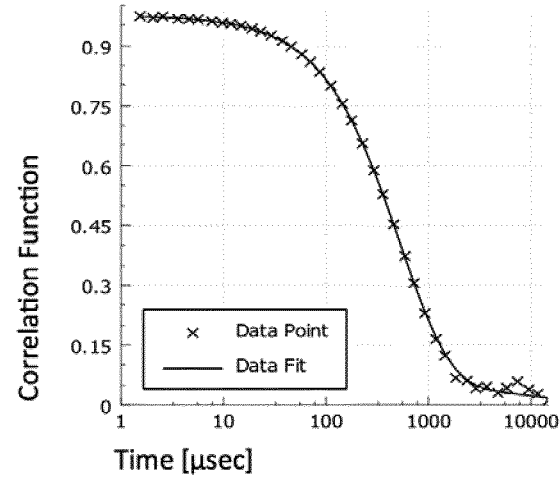

FIG. 3A, FIG. 3B: Graphical representation of liposome size distribution and correlation data. The graphs summarize the liposome size distribution in samples prepared in Example 8, as determined by dynamic light scattering (DLS) with correlation function fits representing diffusion of particles within the sample being measured plotted. FIG. 3A shows the size distribution of liposomes in samples obtained from a single cycle of extrusion, which had a lipid content of 10% by weight. The polydispersity index of these samples was found to be at least 0.2 (PDI>0.2). FIG. 3B shows the size distribution of liposomes in samples obtained from a single cycle of extrusion, which had a lipid content of 30% by weight. The polydispersity index of these samples was found to be less than 0.2 (PDI<0.2).

Figure 4:
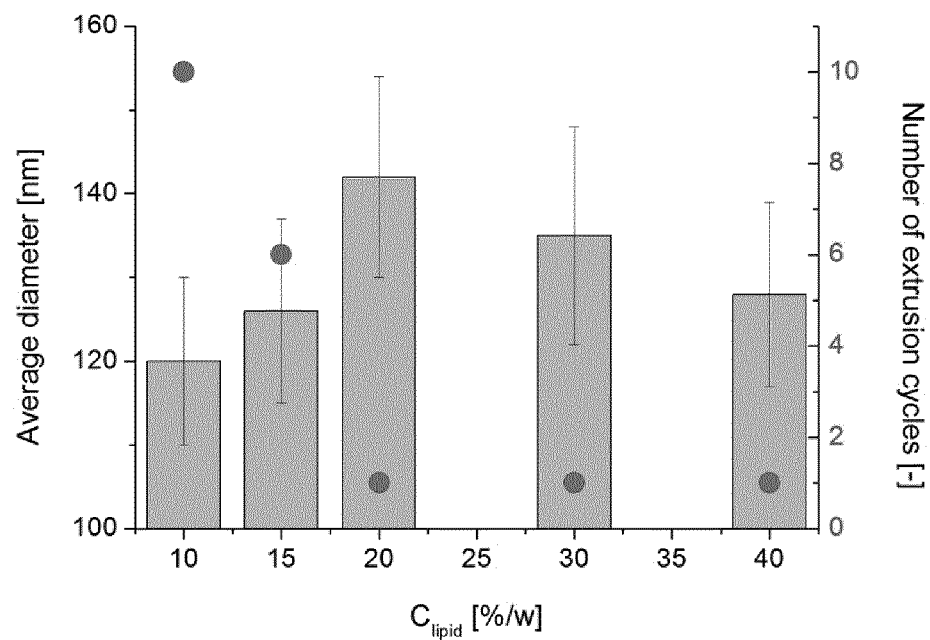

FIG. 4: Graphical representation of liposome size as a function of lipid concentration and number of extrusion cycles at RT. The graph illustrates the liposome sizes in the samples prepared in Example 8 by extrusion carried out at a room temperature, as a function of lipid concentration and the number of extrusion cycles required to obtain samples with a PDI<0.2. For lipid contents ranging from 20-40% by weight, samples with a highly uniform liposome size distribution were obtained already in the first extrusion cycle.

Figure 5:
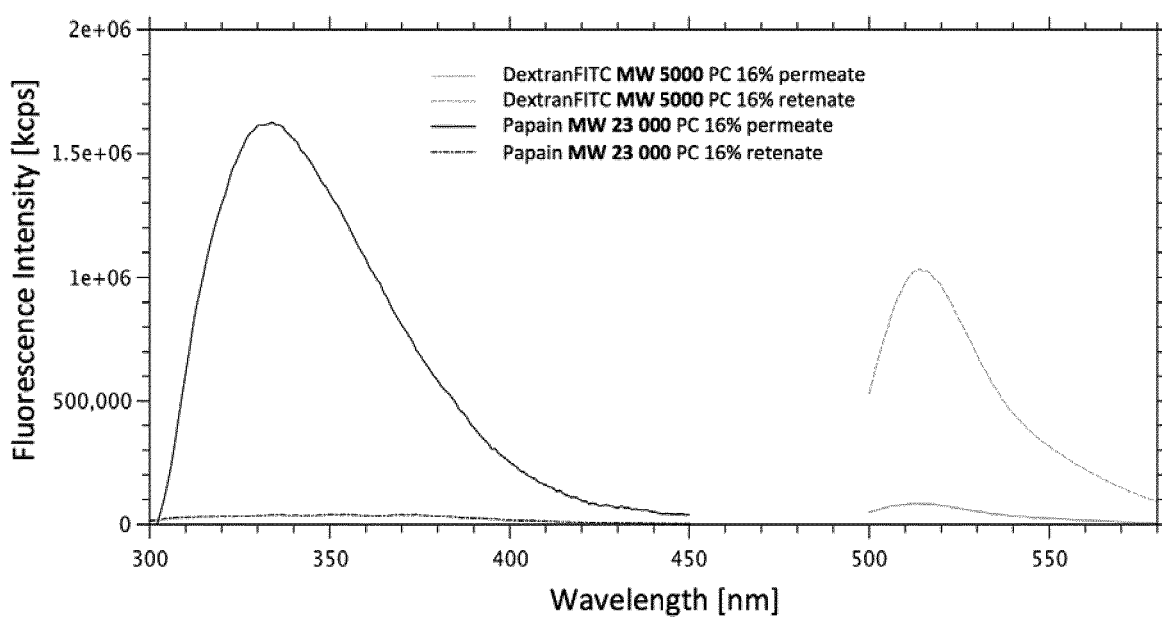

FIG. 5: Graphical representation of the sample emission spectra of UL encapsulated, fluorescent labeled dextran (FITC-label) and papain. The graph illustrates the emission spectra of the permeate and retentate obtained by the ultrafiltration and fractioning of samples described in Example 9. DextranFITC MW 5000 PC 16% permeate: emission spectrum of permeate from samples comprising UL encapsulated FITC-labeled dextran of 5 kDa and an overall phosphatidyl choline (PC) concentration of 16% by weight of the of the sample; DextranFITC MW 5000 PC 16% retentate: emission spectrum of retentate from samples comprising UL encapsulated FITC-labeled dextran of 5 kDa and an overall PC concentration of 16% by weight of the of the sample; Papain MW 23 000 PC 16% permeate: emission spectrum of permeate from samples comprising UL encapsulated papain of 23 kDa and an overall PC concentration of 16% by weight of the of the sample; Papain MW 23 000 PC 16% retentate: emission spectrum of retentate from samples comprising UL encapsulated papain of 23 kDa and an overall PC concentration of 16% by weight of the of the sample.

Figure 6:
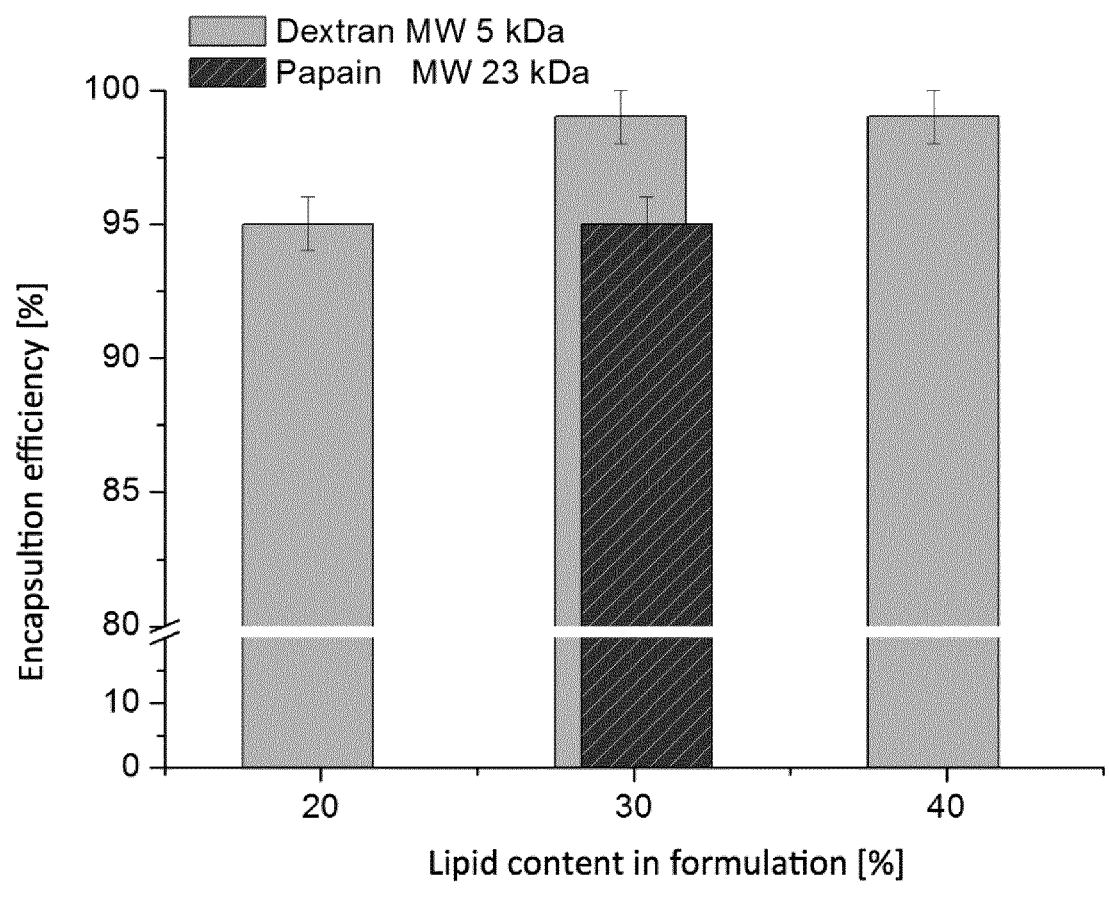

FIG. 6: Graphical representation of the encapsulation efficiency for fluorescent labeled dextran (FITC-label) and papain. The graph illustrates the efficiency of encapsulation of fluorescent labeled dextran with a molecular weight of 5 kDa and papain with a molecular weight of 23 kDa by the method described in Example 9 as a function of lipid concentration in the resulting UL suspension.

Figure 7A:
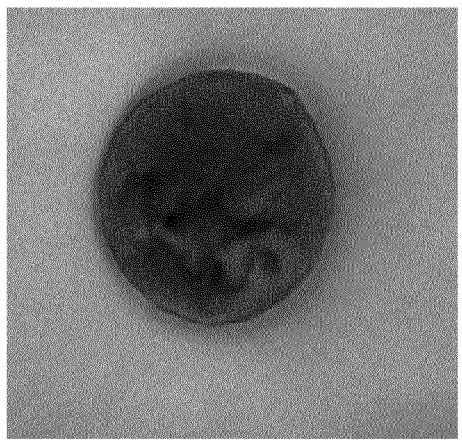
Figure 7B:
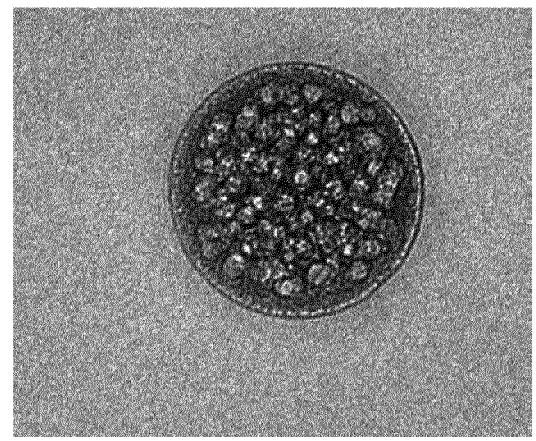

FIG. 7A, 7B: Imaging of samples comprising hydrophilic macromolecules encapsulated within the hydrophilic space of ULs according to the invention. The images were obtained from transmission electron microscopy. FIG. 7A shows UL encapsulated unfractionated heparin. Hydrodynamic diameter of structure: 150 nm. FIG. 7B shows UL encapsulated PVP polymer with covalently bound molecule of chlorine E6 having a molecular weight of 12 kDa. Hydrodynamic diameter of structure: 130 nm.

DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Several documents are cited throughout the text of this specification. Each of the documents cited herein (including all patents, patent applications, scientific publications, manufacturer's specifications, instructions etc.), whether supra or infra, is hereby incorporated by reference in its entirety. Nothing herein is to be construed as an admission that the invention is not entitled to antedate such disclosure by virtue of prior invention.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Throughout this specification and the claims which follow, unless the context requires otherwise, the word "comprise", and variations such as "comprises" and "comprising", are to be understood to imply the inclusion of a stated integer or step or group of integers or steps but not the exclusion of any other integer or step or group of integer or step. As used in this specification and the appended claims, the singular forms "a", "an", and "the" include plural referents, unless the content clearly dictates otherwise.

DETAILED DESCRIPTION OF THE INVENTION

In the following passages different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

In the work leading to the present invention it was surprisingly found that large amounts of hydrophilic compounds can be stably encapsulated within the unilamellar liposomes of the present invention. Specifically, it was surprisingly found by the present inventors that a hydrophilic compound dissolved in a hydrophilic solvent can be encapsulated within the hydrophilic space of a unilamellar liposome (UL) in a concentration of at least 80% of the saturation concentration of said hydrophilic compound in said hydrophilic solvent at 20° C. and 101 kPa in case that said UL comprises propylene glycol or glycerine.

The successful encapsulation of such high amounts of hydrophilic compounds in unilamellar liposomes provides several advantages depending on the application route of said liposomes. When administered parenterally, either by the intravenous or intramuscular route, liposomes can provide controlled "depot" release of encapsulated hydrophilic compound over an extended time period and reduce the side effects of the hydrophilic compound by limiting the concentration of free hydrophilic compound in the bloodstream. Liposomes can alter the tissue distribution and uptake of hydrophilic compounds in a therapeutically favorable way and can increase the convenience of therapy by allowing less frequent compound administration.

Accordingly, the present invention provides in a first aspect a unilamellar liposome (UL) with one lipid bilayer enclosing a hydrophilic space, wherein the UL comprises: (i) at least one hydrophobic compound forming the lipid bilayer, and (ii) propylene glycol or glycerine, and wherein the hydrophilic space comprises at least one hydrophilic compound dissolved in a hydrophilic solvent, and wherein the concentration of the hydrophilic compound in the hydrophilic solvent is at least 80% of the saturation concentration of the hydrophilic compound in the hydrophilic solvent at 20° C. and 101 kPa.

Unilamellar Liposome (UL)

The term "unilamellar liposome" or "UL" as used herein refers to a vesicle composed of a single lipid bilayer, which encloses a hydrophilic space. Said vesicle can be of any shape, including ellipsoids, discoids, pear-shaped vesicles, cup-shaped vesicles, budded vesicles, and spherical vesicles. Preferably, the unilamellar liposome of the present invention is substantially spherical in shape.

The ULs of the present invention may be small unilamellar vesicles (SUVs) having a diameter of up to 100 nm, or large unilamellar vesicles (LUVs) having a diameter of larger than 100 nm up to 1 μm. It is preferred that the diameter of the UL of the present invention is between 50 to 250 nm, between 100 to 200 nm, or between 130 to 150 nm. The term "diameter" as used herein refers to the hydrodynamic diameter, which is to be understood as the size of a hypothetical hard sphere that diffuses in the same fashion as that of the particle being measured. Suitable methods for determining the hydrodynamic diameter of the herein disclosed UL, such as Dynamic Light Scattering (DLS), are know to a person skilled in the art.

The ULs of the invention may be used in therapy, or in the preparation of a medicament, cosmetic product, food additive or disinfectant.

Lipid Bilayer

The term "lipid bilayer" as used herein refers to a closed structure composed of two lipid layers, which are formed by the assembly of hydrophobic compounds.

Hydrophobic Compound

The term "hydrophobic compound" as used herein refers to amphiphilic lipid compounds containing both polar and apolar regions. Preferably, said hydrophobic compound is selected from phospholipids, sphingolipids, and sterols. More preferably, said hydrophobic compound is phosphatidylcholine, even more preferably purified soybean phosphatidylcholine.

In the herein described UL, the apolar chains of the hydrophobic compounds are directed towards the inside of the lipid bilayer facing each other, and thus define a nonpolar region between two polar ones. The thus formed lipophilic inner compartment between the two lipid layers acts as a permeability barrier for hydrophilic substances, both inward and outward. The polar groups of the hydrophobic compounds are positioned towards the surrounding medium as well as towards the inner space of the closed structure formed by the lipid bilayer.

It is preferred that in the UL according to the invention, the weight ratio of the at least one hydrophobic compound forming the lipid bilayer and propylene glycol or glycerine comprised in the UL is in the range of from 2:1 to 1:1. Suitable methods for determining said weight ratio are commonly known to a person skilled in the art, such as ultracentrifugation for compound separation, HPLC-ELSD for hydrophobic compound concentration determination, and gas chromatography (GC) for propylene glycol and glycerine content determination (e.g. see Elmoslemany R M, Abdallah O Y, El-Khordagui L K, Khalafallah N M. *Propylene Glycol Liposomes as a Topical Delivery System for Miconazole Nitrate: Comparison with Conventional Liposomes*. AAPS PharmSciTech. 2012; 13 (2): 723-731. doi: 10.1208/s12249-012-9783-6).

It is also preferred that the UL of the invention comprises the at least one hydrophobic compound in an amount from 15 to 40%, from 16 to 39%, from 17 to 38%, from 18 to 37%, from 19 to 35%, from 20 to 30%, from 21 to 25%, or from 22 to 24% by weight of the UL, and more preferably from 20 to 40% by weight of the UL.

Also preferably, the weight ratio of the at least one hydrophobic compound forming the lipid bilayer and the at least one hydrophilic compound comprised in the hydrophilic space of the herein described UL is in the range of from 100:1 to 1:3, from 50:1 to 1:2, or from 25:1 to 1:1. Said weight ratio in the UL can be determined by any method known to a person skilled in the art, e.g. by hydrophobic compound extraction followed by HPCL-ELSD detection of the hydrophobic compound concentration. Choosing an appropriate analytical method for hydrophilic compound detection depending on said hydrophilic compound's physicochemical properties lies within the ordinary skills of a practitioner.

In an embodiment the UL of the invention is free from charged lipids.

Hydrophilic Space

The term "hydrophilic space" as used to herein refers to the space which is bounded by the polar inner surface of the closed structure formed by the lipid bilayer. The hydrophilic space of the UL according to the invention comprises a hydrophilic solvent and at least one hydrophilic compound which is dissolved in said hydrophilic solvent.

Hydrophilic Solvent

The term "hydrophilic solvent", as used herein, refers to any solvent that is immiscible with octanol. Preferably, said term refers to any solvent with a relative permittivity value within the range of 75.0-80.1 at 20° C. In the herein described method, the hydrophilic solvent may be selected from the group consisting of water, an aqueous buffer, an aqueous salt solution, an aqueous mono- or di-saccharide solution and combinations thereof.

It is preferred that at least 90%, at least 95%, or at least 99% by weight of the hydrophilic solvent is comprised in the hydrophilic space of the UL of the invention. Most preferably, 100% by weight of the hydrophilic solvent is comprised in the hydrophilic space of the UL of the invention.

Hydrophilic Compound

The term "hydrophilic compound" as used herein refers to any compound that has a negative log P value (P=partition-coefficient octanol-water). The partition-coefficient can be determined by any method known in the art (e.g. see J. Sangster: *Octanol-Water Partition Coefficients: Fundamentals and Physical Chemistry*, Vol. 2 of Wiley Series in Solution Chemistry, John Wiley & Sons, Chichester, 1997). Preferably, the hydrophilic compound is selected from the group consisting of ions, proteins, peptides, carbohydrates, natural and synthetic polymers, nucleic acids, nucleic acid derivatives, and combinations thereof.

It is also preferred that the at least one hydrophilic compound is selected from the group consisting of: (i) low molecular weight hydrophilic substances having a molecular weight of from 100 Da to 1500 Da, from 200 Da to 1400 Da, from 300 Da to 1200 Da, or from 500 Da to 1000 Da; and (ii) hydrophilic macromolecules having a molecular weight range of from 1500 Da to 300 kDa, from 2 kDa to 280 kDa, from 5 kDa to 250 kDa, from 10 kDa to 200 kDa or from 50 kDa to 200 kDa.

The concentration of the hydrophilic compound in the hydrophilic solvent comprised in the UL of the invention is at least 80% of the saturation concentration of the hydrophilic compound in the hydrophilic solvent at 20° C. and 101 kPa.

The term "saturation concentration" as used herein means the concentration of the hydrophilic compound in the hydrophilic solvent at 20° C. and 101 kPa at which the hydrophilic solvent can dissolve no more of the hydrophilic compound and additional amounts of said hydrophilic compound will appear as a separate phase, i.e. as a precipitate. Suitable methods for determining the saturation concentration of a hydrophilic compound are commonly known to a person skilled in the art, e.g. the flask method or column elution method according to the OECD guideline for testing water solubility of chemicals (see OECD Guidelines for the Testing of Chemicals, Section 1, Test no. 105—Water solubility).

Preferably, the saturation concentration of the hydrophilic compound in the hydrophilic solvent is in the range from 1 g to 500 g per 1000 ml hydrophilic solvent, more preferably in the range of 10 g to 200 g per 1000 ml hydrophilic solvent.

It is further preferred that the total molar ratio of hydrophilic compounds to hydrophobic compounds comprised in the herein described UL is more than 1:100000.

METHOD OF THE INVENTION

The present inventors further developed a method for high-efficacy encapsulation of hydrophilic compounds within unilamellar liposomes. It was surprisingly found that more than 50% of the total volume of an aqueous phase comprising a hydrophilic compound can be stably encapsulated in ULs by using a polyhydric alcohol selected from propylene glycol and glycerine as a solvent for the hydrophobic compound forming the lipid bilayer.

Accordingly, in a second aspect, the invention relates to a method for the encapsulation hydrophilic compounds in ULs, said method comprising the following steps: providing a lipid solution comprising at least one hydrophobic compound and a polyhydric alcohol selected from propylene glycol and glycerine; providing an aqueous phase comprising at least one hydrophilic compound; preparing a hydrated lipid solution by mixing the lipid solution of (a) with the aqueous phase of (b); and extruding the hydrated lipid solution of (c) at a temperature of less than 80° C., wherein the at least one hydrophobic compound forms a homogenous population of ULs, wherein said ULs comprise more than 50% of the total volume of the aqueous phase. Preferably, said ULs comprise more than 55%, more than 60%, more than 65%, more than 70%, more than 75%, more than 80%, more than 85%, more than 90%, more than 95%, more than 98%; or more than 99% of the total volume of the aqueous phase.

Encapsulation Efficiency

The above-described method of the invention facilitates preparation of a stable UL containing suspension with well-defined size distribution by the simple process of low energy extrusion at room temperature, while providing a high structural stability of the encapsulated hydrophilic compound and a high degree of encapsulation, respectively.

The at least one hydrophilic compound may be encapsulated within ULs by the herein described method with an encapsulation efficiency selected from at least 50%, at least 55%, at least 60%, at least 65%, at least 70%, at least 75%, at least 80%, at least 85%, at least 90%, at least 95%, at least 98%, or at least 99%.

In the context of the present invention the term "encapsulation efficiency" refers to the value of "a" expressed in percent [%], which is determined in accordance with the following formula:

$$a = (C_{tot} - C_{out})/C_{tot}$$

wherein "$C_{out}$" refers to the concentration of hydrophilic compound in that part of the aqueous phase remaining outside the hydrophilic space of the UL in the sample, and "$C_{tot}$" refers to the total concentration of the hydrophilic compound in the sample. "$C_{out}$" and "$C_{tot}$" are determined by spectroscopy.

Efficient encapsulation of hydrophilic compounds by the method of the invention is achieved as a result of a high ratio of the encapsulated volume of aqueous phase comprising at least one hydrophilic compound to the volume of said aqueous phase remaining outside the UL. This means that at least half of the total volume of the aqueous phase provided in step (b) of the herein described method is present inside the liposomes obtained by the herein described method.

Accordingly, the composition obtained from the method of the invention comprises a homogenous population of ULs, wherein said ULs comprise more than 50%, more than 55%, more than 60%, more than 65%, more than 70%, more than 75%, more than 80%, more than 85%, more than 90%, more than 95%, more than 98%, or more than 99% of the total volume of the aqueous phase.

In step (b) of the method of the invention the aqueous phase comprising at least one hydrophilic compound may be prepared by dissolving said at least one hydrophilic compound in a hydrophilic solvent. Preferably, the concentration of the hydrophilic compound in the aqueous phase provided in step (b) is at least 80% of the saturation concentration of the hydrophilic compound in the hydrophilic solvent at 20° C. and 101 kPa. The saturation concentration of the hydrophilic compound in the hydrophilic solvent may be in the range from 1 g to 500 g per 1000 ml hydrophilic solvent, and preferably in the range of 10 g to 200 g per 1000 ml hydrophilic solvent.

Step (b) the inventive method may further comprise adjusting the pH of the aqueous phase, preferably to a pH within the range of from 5.0 to 7.5, from 6.0 to 7.4, or from 7.0 to 7.2. It is preferred that said pH adjustment is performed at a temperature of 20° C. Suitable methods for measuring and adjusting the pH of liquid solutions are known to a person skilled in the art.

In the herein described method it is preferred that the polyhydric alcohol is comprised in the hydrated lipid solution of step (c) in a concentration of from 5 to 30%, from 10 to 25%, from 15 to 22%, or from 18 to 20% by weight of the hydrated lipid solution.

Hydrophobic Compound Concentration

It was further found by the present inventors that if a high concentration of the at least one hydrophobic compound is comprised in the hydrated lipid solution prepared in step (c) of the method of the invention an UL suspension is obtained which is densely packed with the lipid bilayers of said ULs. Accordingly, the overall concentration of the at least one hydrophobic compound in the hydrated lipid solution of step (c) may be from 15 to 40%, from 16 to 39%, from 17 to 38%, from 18 to 37%, from 19 to 35%, from 20 to 30%, from 21 to 25%, or from 22 to 24% by weight of said hydrated lipid solution.

It is particularly preferred that the overall concentration of the at least one hydrophobic compound in the hydrated lipid solution of step (c) is from 20 to 40% by weight of said hydrated lipid solution, from 20 to 30% by weight of said hydrated lipid solution, or from 30 to 40% by weight of said hydrated lipid solution. It was found by the present inventors that a single extrusion cycle of a thus concentrated UL suspension further enhances the encapsulation efficiency of the herein described method to up to 99% and achieves a high viscosity of the UL suspension of not less than 4000 cPs (6 RPM RT) without the use of additional gelling or thickening agents. Preferably, a viscosity of the UL suspension of at least 5000 cPs, at least 7000 cPs, or at least 10000 cPs (6 RPM RT) is achieved.

The at least one hydrophobic compound may be selected from phospholipids, sphingolipids or sterols. Preferably, the at least one hydrophobic compound may be selected from phosphatidycholine, more preferably from purified soybean phosphatidylcholine. In an embodiment the hydrated lipid solution of step (c) is free from charged lipids.

Extrusion

Extrusion of the hydrated lipid solution of (c) in step (d) may be performed at a temperature of less than 80° C., less than 60° C., or less than 40° C.

It was surprisingly found that the method of the invention achieves encapsulation of hydrophilic macromolecules in the herein described ULs with an efficiency exceeding 95% already after a single extrusion cycle at room temperature.

Accordingly, it is preferred that step (d) of the herein described method comprises extruding the hydrated lipid solution of (c) at a temperature of less than 30° C., and more preferably at room temperature (20° C.). It is further preferred that the method of the invention comprises a single extrusion cycle. Most preferably, step (d) of the herein described method comprises extruding the hydrated lipid solution of (c) at room temperature (20° C.) in a single extrusion cycle.

The term "extrusion cycle" as used herein refers to one pass of the hydrated lipid solution of (c) through a polycarbonate filter with a pore diameter of 100 nm.

Further Method Steps

The extrusion step (d) of the herein described method may be followed by a further step (f) of removing glycerol or propylene glycol from the UL containing suspension resulting from the extrusion step (d). Preferably, said removal of the polyhydric alcohol is accomplished by ultrafiltration. In a particularly preferred embodiments, the UL containing suspension resulting from the extrusion step (d) is applied to an ultrafiltration system (for example, MicroKros MWCO 70 kD for laboratory scale or commercially available cassettes for larger preparations) and subsequently washed with an isosmotic aqueous phase. The amount of polyhydric alcohol remaining in the liposome suspension after the ultrafiltration step is proportional to the volume fraction of the sample and the applied aqueous phase. Preferably, said amount is less than 1%, less than 0.8%, less than 0.5%, less than 0.4%, less than 0.3%, less than 0.2%, or less than 0.1% by weight of the UL containing suspension.

The method of the invention may comprise a further step of diluting the UL containing suspension resulting from step (d) or (e), preferably by adding saline solution, more preferably sterile saline solution.

Alternatively, said further method step may comprise lyophilization or spray-drying the UL containing suspension resulting from step (d) or (e) in order to provide a solid liposome-containing composition, such as a liposome powder.

Excipients

The method of the invention may further comprise adding at least one excipient, which may be selected form the group consisting of: buffering agents, osmotically active agents, preservatives, antioxidants, flavoring agents, aromatic agents, and combinations thereof. It is preferred that said osmotic agents are selected from monovalent salts or sugars, more preferably from sodium chloride and sucrose. It is further preferred that the method of the invention comprises adding an osmotic agent in an amount such that an osmolarity of the final product in the range of 30 mOsm to 400 mOsm is obtained.

Compositions of the Invention

In a third aspect the invention provides a composition comprising at least one UL according to the herein described invention. In a fourth aspect, the invention provides a composition prepared by the herein described method.

In the context of the present invention the term "composition" refers to both the composition according to the third aspect and the composition according to the fourth aspect, respectively, and includes liquid, semi-solid and solid compositions. The composition of the invention may be a liquid composition, preferably an aqueous liquid composition, such as an aqueous dilution or suspension, or a semi-solid composition such as an ointment or a gel.

The composition of the invention may also be a solid composition, preferably a powder composition, such as a spray-dried or lyophilized powder composition.

The herein described composition may be selected from a pharmaceutical composition, cosmetic composition, food composition, food additive composition, or disinfectant composition. In case that the composition of the invention is a pharmaceutical composition, it is preferred that the hydrophilic compound is a pharmaceutical active agent or drug compound. The herein described composition may further comprise at least one excipient.

Preferably, said excipient is selected form the group consisting of: buffering agents, osmotically active agents, preservatives, antioxidants, flavoring agents, aromatic agents, and combinations thereof; preferably wherein said osmotic agents are selected from monovalent salts or sugars, more preferably from sodium chloride and sucrose.

Preferably, the composition of the invention has at least one of the following properties: (i) a pH within the range of from 5.0 to 7.5, from 6.0 to 7.4, or from 7.0 to 7.2; (ii) an osmolarity in the range of from 30 mOsm to 400 mOsm, from 40 mOsm to 300 mOsm, or from 50 mOsm to 200 mOsm; and/or (iii) a total molar ratio of the hydrophilic compounds to the hydrophobic compounds of between $10^{-5}$ and 1.

It is further preferred that the herein described composition has a viscosity of at least 4000 cPs (6 RPM RT), at least 5000 cPs (6 RPM RT), at least 7000 cPs (6 RPM RT), or at least 10000 cPs (6 RPM RT).

Use of UL and Composition of the Invention

The herein described unilamellar liposome (UL) or composition may be used as a medicament, a cosmetic product, a food additive or a disinfectant, or in the preparation of a medicament, a cosmetic product, a food additive or a disinfectant, respectively. In an embodiment, the UL or composition of the invention is used in therapy.

The herein described composition may be used without further modifications as a dermatological or cosmetic product in the form of an ointment.

The herein described composition may also be used in diluted form. If the hydrophilic substance encapsulated in ULs is intended for systemic use as a medicinal product, the composition of the invention is preferably diluted with an isotonic solution, which does not alter the amount of hydrophilic compound encapsulated within the ULs. Such diluted UL suspensions can be used for administration of peptides, complete proteins, polymers, sugars or nucleic acids in therapeutic applications. To date, the pharmaceutical use of these compounds is limited due to their immediate removal from physiological fluids. This is particularly relevant in oral administration, where the proteins, polymers, sugars or nucleic acids are hydrolyzed during digestion.

Accordingly, in sum, the main obstacles in the development and therapeutic application of biological drugs are overcome by the present invention.

The invention is described by way of the following examples which is to be construed as merely illustrative and not limitative of the scope of the invention.

Example 1

1000 mg of Phospholipon 90G (Lipoid AG) were dissolved in 750 mg propylene glycol (Chempur) while stirring (4 h, RT) until a homogeneous lipid yellow solution was obtained, and then mixed with 3250 mg of an aqueous phase containing 5 mg of fluorescent-labeled dextran (MW 5 kDa) buffered with phosphate buffer (0.01 M, pH 7.2). The resulting mixture was extruded through a polycarbonate filter with a pore diameter of 100 nm in one cycle.

As a result a liposome suspension containing a lipid concentration of 20% per weight of said suspension was obtained, wherein 96% of the labeled dextran was encapsulated within unilamellar liposomes (ULs).

Example 2

1500 mg of Phospholipon 90G (Lipoid AG) were dissolved in 1000 mg propylene glycol (Chempur) with stirring (4 h, RT) until a homogeneous lipid yellow solution was obtained, and then mixed with 2500 mg of an aqueous phase containing 5 mg of fluorescent-labeled dextran (MW 5 kDa) buffered with phosphate buffer (0.01 M, pH 7.2). The resulting mixture was extruded through a polycarbonate filter with a pore diameter of 100 nm in one cycle.

As a result a liposome suspension containing a lipid concentration of 30% per weight of said suspension was obtained, wherein 96% of the labeled dextran was encapsulated within unilamellar liposomes (ULs).

Example 3

2000 mg of Phospholipon 90G (Lipoid AG) were dissolved in 1000 mg propylene glycol (Chempur) with stirring (4 h, RT) until a homogeneous lipid yellow solution was obtained, and then mixed with 2000 mg of an aqueous phase containing 5 mg of fluorescently labeled dextran (MW 5 kDa) buffered with phosphate buffer (0.01 M, pH 7.2). The resulting mixture was extruded through a polycarbonate filter with a pore diameter of 100 nm in one cycle.

As a result a liposome suspension containing a lipid concentration of 40% per weight of said suspension was obtained, wherein 99% of the labeled dextran was encapsulated within unilamellar liposomes (ULs).

Example 4

1500 mg of Phospholipon 90G (Lipoid AG) were dissolved in 1000 mg propylene glycol (Chempur) with stirring (4 h, RT) until a homogeneous lipid yellow solution was obtained, and then mixed with 2500 mg of an aqueous phase containing 50 mg papain (MW 23 kDa) buffered with phosphate buffer (0.01 M, pH 7.2). The resulting mixture was extruded through a polycarbonate filter with a pore diameter of 100 nm in one cycle.

As a result a liposome suspension containing a lipid concentration of 30% per weight of said suspension was obtained, wherein 99% of the papain was encapsulated within unilamellar liposomes (ULs).

Example 5

A highly concentrated vitamin C product for use as an additive or dietary supplement in the treatment of cancer was prepared having the following ingredients:

| Item | Name | Amount [mg] |
|---|---|---|
| 1. | Purified soybean phosphatidylcholine | 210.0 |
| 2. | Propylene glycol | 180.0 |
| 3. | Vitamin C | 210.0 |
| 4. | EDTA | 10.0 |
| 5. | Phosphate buffer | 380.0 |
| 6. | Natural aroma | 5.0 |
| 7. | Sweetening substance | 5.0 |
| | Total: | 1000.0 |

The product was prepared by dissolving 210 mg Phospholipon 90G (Lipoid AG) in 180 mg propylene glycol (Chempur) and stirring this mixture (4 h, RT, 60 RPM) until a homogeneous lipid yellow solution was obtained. Said solution was mixed (12 h, RT, 200 RPM) with 590 mg of an aqueous phase containing 210 mg vitamin C buffered with phosphate buffer (0.01 M, pH 7.2). The resulting mixture was extruded through a polycarbonate filter with a pore diameter of 100 nm in one cycle. EDTA, natural aroma and a sweetening substance were sequentially added and stirred (0.5 h, RT, 60 RPM) in order to obtain the final product.

Example 6

A highly concentrated iron formulation for use as an additive or dietary supplement in the treatment of anemia was prepared having the following ingredients:

| Item | Name | Amount [mg] |
|---|---|---|
| 1. | Purified soybean phosphatidylcholine | 220.0 |
| 2. | Propylene glycol | 180.0 |
| 3. | Iron (III) diphosphate | 20.0 |
| 4. | Vitamin E | 10.0 |
| 5. | Phosphate buffer | 560.0 |
| 6. | Natural aroma | 5.0 |
| 7. | Sweetening substance | 5.0 |
| | Total: | 1000.0 |

The product was prepared by dissolving 220 mg Phospholipon 90G (Lipoid AG) in 180 mg propylene glycol (Chempur) and stirring this mixture (4 h, RT, 60 RPM) until a homogeneous lipid yellow solution was obtained. Said solution was mixed (12 h, RT, 200 RPM) with 580 mg of an aqueous phase containing 20 mg iron(III)diphosphate buffered with phosphate buffer (0.01 M, pH 7.2). The resulting mixture was extruded through a polycarbonate filter with a pore diameter of 100 nm in one cycle. Vitamin E as an antioxidant, natural aroma, and a sweetening substance were sequentially added and stirred (0.5 h, RT, 60 RPM) in order to obtain the final product.

Example 7

A medicinal product for use in gene therapy was prepared having the following ingredients:

| Item | Name | Amount [mg] |
|---|---|---|
| 1. | Phosphatidylcholine | 240.0 |
| 2. | DOTAP | 10.0 |
| 3. | DOPE | 20.0 |
| 4. | Propylene glycol | 200.0 |
| 5. | DNA | 20.0 |
| 6. | PBS | 510.0 |
| | Total: | 1000.0 |

The product was prepared by dissolving 240 mg phosphatidylcholine, 10 mg N-[1-(2,3-dioleoyloxy)propyl]-N,NJ,N-trimethylammonium methyl-sulfate (DOTAP) and 20 mg 1,2-dioleoyl-sn-glycero-3-phosphoethanolamine (DOPE) in 200 mg propylene glycol (Chempur) and stirred (4 h, RT, 60 RPM) until a homogeneous lipid yellow solution was obtained. Said solution was mixed (12 h, RT, 200 RPM) with 530 mg of an aqueous phase containing 20 mg deoxyribonucleic acid (DNA) buffered with phosphate buffered saline 1×(PBS). The resulting mixture was extruded through a polycarbonate filter with a pore diameter of 100 nm in one cycle. The resulting product was lyophilized or diluted in saline for direct administration.

Example 8

For optimizing the production process of unilamellar liposomes (UL) several liposome containing samples were prepared using the formulation and process parameters shown in Table 1, and viscosity and size distribution in these samples were determined.

TABLE 1

Summary of formulation and process parameters of tested liposome samples

| Sample | Phosph-atidylcholine | Propylene glycol | Extrusion | Pore diameter | Number of extrusion cycles (PDI < 0.2) |
|---|---|---|---|---|---|
| 1 | 1.0 g | 2.0 g | NO | — | — |
| 2 | 1.0 g | 2.0 g | YES | 100 nm | 10 |
| 3 | 1.5 g | 2.0 g | NO | — | — |
| 4 | 1.5 g | 2.0 g | YES | 100 nm | 6 |
| 5 | 2.0 g | 2.0 g | NO | — | — |
| 6 | 2.0 g | 2.0 g | YES | 100 nm | 1 |
| 7 | 2.5 g | 2.0 g | NO | — | — |
| 8 | 2.5 g | 2.0 g | YES | 100 nm | 1 |

In the first step of the production process of unilamellar liposome (UL) containing samples a lipid solution was prepared by stirring a mixture of phosphatidylcholine and propylene glycol and incubating said mixture for several hours at room temperature until total dissolution of the phosphatidylcholine. To the obtained clear yellow lipid solution distilled water was added in an amount to obtain a final sample weight of 10 g. The sample was vigorously mixed until a homogeneous, white suspension of phospholipid was obtained.

The obtained suspension of multilamellar liposomes (MLV) was divided into three equal batches. One batch was put through a viscosity test (uncalibrated batch). The two other batches were calibrated by extrusion through polycarbonate filters having a pore diameter of 100 nm. The extrusion process was carried out either at room temperature (RT) or at 70° C., respectively, until a homogeneous size distribution of the resulting unilamellar liposomes (UL) in the samples was obtained.

The viscosities of the obtained liposome containing samples were determined by using a Bruker rheometer equipped with the cone-plate measuring system. A small amount of sample (0.1-0.2 g) was placed into a thermostated measuring chamber and characterized by measuring the change in viscosity in relation to the rotation speed of the cone. The measurement was performed at a room temperature (20° C.). The results of these viscosity measurements are shown in FIG. 1 and FIG. 2.

Further, the size distribution of the liposomes in the obtained samples was determined by dynamic light scattering (DLS) using a Malvern ZetaSizer Nano ZS instrument, after diluting the samples with distilled water in a ratio of 1:100. The results of size determination are shown in FIG. 3A, FIG. 3B and FIG. 4.

Results

As a result of optimizing the production process of unilamellar liposomes (ULs), it was found that the formation of ULs already occurs after low pressure extrusion at room temperature. Further, it was found to be preferable that the amount of lipid in the extruded samples is at least 20% by weight. Setting said lipid concentration to greater than or equal to 20% by weight was further found to facilitate obtaining a monodisperse population of liposomes (PDI<0.2) by a single pass of a sample through a polycarbonate filter, as opposed to samples containing lower amounts of lipids.

Example 9

For demonstrating the high efficiency of the inventive encapsulation method for hydrophilic macromolecules, samples were prepared according to Examples 1 to 4 by mixing a solution of lipid in propylene glycol with an aqueous solution of a fluorescent labeled hydrophilic polymer (FITC-labeled dextran of 5 kDa) or protein (papain with the molecular weight of 23 kDa), respectively, and extruding the resulting suspensions through a polycarbonate filter with a pore diameter of 100 nm. The lipid concentration in the resulting UL suspensions ranged from 20% to 40% by weight of said suspensions.

The size of the ULs was verified using the DLS technique as described in Example 8 after diluting the sample with distilled water in the ratio of 1:100.

The concentrations of the UL encapsulated fluorescent labeled polymer or protein were determined by spectroscopy. Therefore, the samples were subjected to ultrafiltration via a Biomax-50 filtration cassette (Merck Millipore) with a cut-of range 140-300 kDa in order to determine the concentration of hydrophilic compound in both compartments, namely outside the liposomes (permeate fraction) and inside the liposomes (retentate fraction). The steady-state fluorescence emission spectra were measured with a Thermo Scientific Nicolet Evolution 100 UV-VIS spectrofluorimeter. The excitation wavelength was set to 280 nm and 490 nm for papain and fluorescein-labeled dextran (FITC-dextran), respectively.

The encapsulation efficiency was determined in accordance with the formula provided herein above. Briefly, the encapsulation efficiency "a" expressed in percent [%], was determined in accordance with the following formula:

$$a = (C_{tot} - C_{out})/C_{tot}$$

wherein "$C_{out}$" determines the concentration of hydrophilic compound in that part of the aqueous phase remaining outside the hydrophilic space of the UL in the sample, and "$C_{tot}$" determines the total concentration of the hydrophilic compound in the sample.

Results

In all of the samples a homogenous population of ULs having an average size of about 100 nm and a PDI<0.2 was obtained after a single extrusion cycle, wherein nearly 100% of the dextran or papain was encapsulated within the ULs, respectively. The sample emission spectra of the filtrate (permeate) and the aqueous fraction encapsulated within the ULs (retentate) for both the samples containing papain and fluorescent-labeled dextran, respectively, are shown in FIG. 5.

Specifically, the method of the invention was shown to achieve encapsulation of these hydrophilic macromolecules in the said ULs with an efficiency exceeding 95%. Calculated encapsulation efficiencies are shown on FIG. 6 as a function of lipid concentration in the sample.

Example 10

In order to confirm the high efficiency of the herein presented methodology for encapsulating hydrophilic macromolecules as well as the integrity of the obtained structures, imaging of UL formulations according to the invention containing unfractionated heparin and PVP with a covalently bonded molecule of chlorine E6, respectively, was carried out using transmission electron microscopy (see FIG. 7). The resulting images confirm the effectiveness of encapsulation of hydrophilic macromolecules in the UL of the herein described invention and the high efficiency of the encapsulation method described herein.

Example 11

For further demonstrating the high efficiency of the inventive encapsulation method for hydrophilic macromolecules, 1000 mg of Phospholipon 90G (Lipoid AG) were dissolved in 1000 mg glycerin (PCC, Poland) while stirring (4 h, RT) until a homogeneous lipid yellow solution was obtained, and then mixed with 2000 mg of an aqueous solution containing 10 mg of albumin (MW over 66 kDa) in 0.1 M NaCl. The encapsulation efficiency was determined as described in Example 9 above.

As a result, a UL suspension containing a lipid concentration of 25% per weight of said suspension was obtained, wherein 83% of the albumin was encapsulated within unilamellar liposomes (ULs).

Example 12

For further demonstrating the high efficiency of the inventive encapsulation method for hydrophilic macromolecules, 25 g Phospholipon 90G (Lipoid AG) was dissolved in 25 g glycerin (PCC, Poland) while stirring (4 h, RT) until a homogeneous lipid yellow solution was obtained, and then mixed with 50 g of the aqueous phase containing 0.5% w/w heparin in 0.1 M NaCl. The resulting mixture was extruded through a polycarbonate filter with a pore diameter of 100 nm in one cycle. In order to evaluate the encapsulation efficiency, the resulting UL suspensions were subjected to ultrafiltration via a Biomax-50 filtration cassette (Merck Millipore) with a cut-of range 140-300 kDa in order to determine the concentration of hydrophilic compound in both compartments, namely outside the liposomes (permeate fraction) and inside the liposomes (retentate fraction). The concentrations of detector and the UL encapsulated heparin were determined using HPLC equipped with the ELSD detector and SEC column.

As a result liposome suspensions containing a lipid concentration of 25% per weight of said suspension was obtained, wherein 56% of the heparine was encapsulated within unilamellar liposomes (ULs).

Example 13

For further demonstrating the high efficiency of the inventive encapsulation method for hydrophilic macromolecules, 30 g Phospholipon 90G (Lipoid AG) was dissolved in 20 g glycerin (PCC, Poland) while stirring (4 h, RT) until a homogeneous lipid yellow solution was obtained, and then mixed with 50 g of the aqueous phase containing 0.5% w/w heparin in 0.1 M NaCl. The resulting mixture was extruded through a polycarbonate filter with a pore diameter of 100 nm in one cycle. In order to evaluate the encapsulation efficiency, the resulting UL suspensions were subjected to ultrafiltration via a Biomax-50 filtration cassette (Merck Millipore) with a cut-of range 140-300 kDa in order to determine the concentration of hydrophilic compound in both compartments, namely outside the liposomes (permeate fraction) and inside the liposomes (retentate fraction). The concentrations of detector and the UL encapsulated heparin were determined using HPLC equipped with the ELSD detector and SEC column.

As a result liposome suspensions containing a lipid concentration of 30% per weight of said suspension was obtained, wherein 80% of the heparine was encapsulated within unilamellar liposomes (ULs), respectively.

The invention claimed is:
1. A unilamellar liposome (UL) with one lipid bilayer enclosing a hydrophilic space, wherein the UL comprises:
 (i) at least one hydrophobic compound forming the lipid bilayer, and
 (ii) propylene glycol or glycerine,
and wherein the hydrophilic space comprises nucleic acids or nucleic acid derivatives dissolved in a hydrophilic solvent, and wherein the concentration of the nucleic acids or nucleic acid derivatives in the hydrophilic solvent is at least 80% of the saturation concentration of the nucleic acids or nucleic acid derivatives in the hydrophilic solvent at 20° C. and 101 kPa.

2. The UL according to claim 1, wherein the weight ratio of the at least one hydrophobic compound forming the lipid bilayer and propylene glycol or glycerine is in the range of from 2:1 to 1:1.

3. The UL according to claim 1, wherein the weight ratio of the at least one hydrophobic compound forming the lipid bilayer and the nucleic acids or nucleic acid derivatives is in the range of from 100:1 to 1:3, from 50:1 to 1:2, or from 25:1 to 1:1.

4. The UL according to claim 1, wherein the UL comprises the at least one hydrophobic compound in an amount from 15 to 40% by weight of the UL.

5. The UL according to claim 1, wherein the nucleic acids or nucleic acid derivatives have a molecular weight range of from 1000 Da to 300 kDa, from 1500 Da to 300 kDa, from 2 kDa to 280 kDa, from 5 kDa to 250 kDa, from 10 kDa to 200 kDa, or from 50 kDa to 200 kDa.

6. The UL according to claim 1, wherein the saturation concentration of the nucleic acids or nucleic acid derivatives in the hydrophilic solvent is in the range from 1 g to 200 g per 1000 ml hydrophilic solvent.

7. The UL according to claim 1, wherein the hydrophilic solvent is selected from the group consisting of water, aqueous buffer, aqueous salt solution, aqueous mono- or di-saccharide solution and combinations thereof.

8. A liquid composition comprising at least one UL according to claim 1.

9. The liquid composition according to claim 8, wherein said composition has at least one of the following properties:
 (i) a pH within the range of from 6.0 to 7.5, from 6.0 to 7.4, or from 7.0 to 7.2;
 (ii) an osmolarity in the range of from 30 mOsm to 400 mOsm, from 40 mOsm to 300 mOsm, or from 50 mOsm to 200 mOsm;
 (iii) a total molar ratio of the nucleic acids or nucleic acid derivatives to the hydrophobic compounds of between $10^{-5}$ and 1;
 preferably wherein said composition is an aqueous composition.

10. The liquid composition according to claim 8, further comprising at least one excipient, preferably wherein said excipient is selected form the group consisting of: buffering agents, osmotically active agents, preservatives, antioxidants, and combinations thereof; preferably wherein said osmotic agents are selected from monovalent salts or sugars, more preferably from sodium chloride and sucrose.

11. A method for encapsulation of nucleic acids or nucleic acid derivatives in ULs, said method comprising the following steps:
 (a) providing a lipid solution comprising at least one hydrophobic compound and a polyhydric alcohol selected from propylene glycol and glycerine;
 (b) providing an aqueous phase comprising nucleic acids or nucleic acid derivatives;
 (c) preparing a hydrated lipid solution by mixing the lipid solution of (a) with the aqueous phase of (b); and
 (d) extruding the hydrated lipid solution of (c) at a temperature of less than 80° C., wherein the at least one hydrophobic compound forms a homogenous population of ULs, wherein said ULs comprise more than 50% of the total volume of the aqueous phase.

12. The method according to claim 11, wherein the nucleic acids or nucleic acid derivatives are encapsulated within the ULs with an encapsulation efficiency selected from at least 50%, at least 55%, at least 60%, at least 65%, at least 70%, at least 75%, at least 80%, at least 85%, at least 90%, at least 95%, at least 98%; or at least 99%.

13. The method according to claim 11, wherein the polyhydric alcohol is comprised in the hydrated lipid solution of step (c) in a concentration of from 5 to 30%, from 10 to 25%, from 15 to 22%, or from 18 to 20% by weight of the hydrated lipid solution.

14. The method according to claim 11, wherein the overall concentration of the at least one hydrophobic compound in the hydrated lipid solution of step (c) is from 15 to 40%, from 16 to 39%, from 17 to 38%, from 18 to 37%, from 19 to 35%, from 20 to 30%, from 21 to 25%, or from 22 to 24% by weight of said hydrated lipid solution, and preferably from 20 to 40% by weight of said hydrated lipid solution.

15. The method according to claim 11, wherein the at least one hydrophobic compound is selected from phospholipids, sphingolipids or sterols, preferably from phosphatidycholine, and more preferably from purified soybean phosphatidylcholine.

16. The method according to claim 11, wherein step (b) comprises adjusting the pH of the aqueous phase, preferably to a pH within the range of from 6.0 to 7.5, from 6.0 to 7.4, or from 7.0 to 7.2.

17. The method according to claim 11, said method comprising a further step (e) wherein the polyhydric alcohol selected from propylene glycol and glycerine is removed from the extruded hydrated lipid solution resulting from step (d), preferably wherein said polyhydric alcohol is removed from said extruded hydrated lipid solution by ultrafiltration.

18. A unilamellar liposome (UL) prepared by the method according to claim 11.

19. A method of treatment comprising administration of the UL according to claim 1 to a patient in need thereof.

* * * * *